United States Patent
Simon et al.

(10) Patent No.: US 8,838,199 B2
(45) Date of Patent: *Sep. 16, 2014

(54) METHOD AND APPARATUS FOR VIRTUAL DIGITAL SUBTRACTION ANGIOGRAPHY

(75) Inventors: David A Simon, Boulder, CO (US); Kevin Foley, Germantown, TN (US); Mark Hunter, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 2200 days.

This patent is subject to a terminal disclaimer.

(21) Appl. No.: 11/057,528

(22) Filed: Feb. 14, 2005

(65) Prior Publication Data
US 2005/0165292 A1    Jul. 28, 2005

Related U.S. Application Data

(63) Continuation of application No. 10/116,631, filed on Apr. 4, 2002, now Pat. No. 6,990,368.

(51) Int. Cl.
*A61B 5/05*    (2006.01)

(52) U.S. Cl.
USPC ........... 600/407; 600/411; 600/424; 600/425; 600/426; 600/427; 600/428; 600/429; 378/20; 378/21; 378/62; 378/165; 378/205; 382/107; 382/128

(58) Field of Classification Search
USPC ........ 600/407, 411, 424–429; 378/20–21, 62, 378/165, 205; 382/107, 128
See application file for complete search history.

(56) References Cited

U.S. PATENT DOCUMENTS

| | | | |
|---|---|---|---|
| 1,576,781 | A | 3/1926 | Philips |
| 1,735,726 | A | 11/1929 | Bornhardt |
| 2,407,845 | A | 9/1946 | Nemeyer |
| 2,650,588 | A | 9/1953 | Drew |
| 2,697,433 | A | 12/1954 | Zehnder |
| 3,016,899 | A | 1/1962 | Stenvall |
| 3,017,887 | A | 1/1962 | Heyer |
| 3,061,936 | A | 11/1962 | Dobbeleer |
| 3,073,310 | A | 1/1963 | Mocarski |
| 3,109,588 | A | 11/1963 | Polhemus et al. |
| 3,294,083 | A | 12/1966 | Alderson |

(Continued)

FOREIGN PATENT DOCUMENTS

| | | |
|---|---|---|
| CA | 964149 | 3/1975 |
| DE | 3042343 | 6/1982 |

(Continued)

OTHER PUBLICATIONS

Meijeiring, Image Enhancement in Digital X-Ray Angiography, thesis, 2000.*

(Continued)

*Primary Examiner* — Long V. Le
*Assistant Examiner* — Bo J Peng
(74) *Attorney, Agent, or Firm* — Harness, Dickey

(57) ABSTRACT

A method and apparatus for allowing determination of patient position change relative to an imaging device and/or allowing digital subtraction in an operative position. The system can include devices for determining a position of a patient at various times and comparing the various positions of the patient. Further, a digital subtraction may be performed if the patient change is not above a threshold value and/or if motion correction can occur.

50 Claims, 6 Drawing Sheets

(56) References Cited

U.S. PATENT DOCUMENTS

| | | |
|---|---|---|
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,847,157 A | 11/1974 | Caillouette et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,068,556 A | 1/1978 | Foley |
| 4,071,456 A | 1/1978 | McGee et al. |
| 4,117,337 A | 9/1978 | Staats |
| 4,173,228 A | 11/1979 | Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,259,725 A | 3/1981 | Andrews et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,335,427 A | 6/1982 | Hunt et al. |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,360,028 A | 11/1982 | Barbier et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,465,069 A | 8/1984 | Barbier et al. |
| 4,467,146 A | 8/1984 | Lassaux |
| 4,485,815 A | 12/1984 | Amplatz |
| 4,506,676 A | 3/1985 | Duska |
| 4,533,946 A | 8/1985 | Yasuhara et al. |
| 4,541,106 A | 9/1985 | Belanger et al. |
| 4,543,959 A | 10/1985 | Sepponen |
| 4,544,948 A | 10/1985 | Okazaki |
| 4,544,949 A | 10/1985 | Kurihara |
| 4,548,208 A | 10/1985 | Niemi |
| 4,559,557 A | 12/1985 | Keyes et al. |
| 4,571,834 A | 2/1986 | Fraser et al. |
| 4,572,198 A | 2/1986 | Codrington |
| 4,574,265 A | 3/1986 | Kaiser |
| 4,575,752 A | 3/1986 | Honda |
| 4,583,538 A | 4/1986 | Onik et al. |
| 4,584,577 A | 4/1986 | Temple |
| 4,586,926 A | 5/1986 | Osborne |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,628,355 A | 12/1986 | Ogura et al. |
| 4,638,798 A | 1/1987 | Shelden et al. |
| 4,639,867 A | 1/1987 | Suzuki et al. |
| 4,642,786 A | 2/1987 | Hansen |
| 4,645,343 A | 2/1987 | Stockdale et al. |
| 4,649,504 A | 3/1987 | Krouglicof et al. |
| 4,649,561 A | 3/1987 | Arnold |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,689,670 A | 8/1987 | Okazaki |
| 4,692,864 A | 9/1987 | Shimoni et al. |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,724,110 A | 2/1988 | Arnold |
| 4,727,565 A | 2/1988 | Ericson |
| RE32,619 E | 3/1988 | Damadian |
| 4,729,379 A | 3/1988 | Ohe |
| 4,733,969 A | 3/1988 | Case et al. |
| 4,736,398 A | 4/1988 | Graeff et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,764,944 A | 8/1988 | Finlayson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A * | 12/1988 | Crum et al. .................. 600/409 |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,213 A | 4/1989 | Cline et al. |
| 4,821,731 A | 4/1989 | Martinelli et al. |
| 4,822,163 A | 4/1989 | Schmidt |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,825,091 A | 8/1989 | Breyer et al. |
| 4,860,331 A | 8/1989 | Williams et al. |
| 4,862,893 A | 9/1989 | Martinelli |
| 4,869,247 A | 9/1989 | Howard, III et al. |
| 4,870,692 A * | 9/1989 | Zuiderveld et al. ........... 382/107 |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |

(56) References Cited

U.S. PATENT DOCUMENTS

| | | |
|---|---|---|
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,578 A | 4/1991 | Greer et al. |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,454 A | 12/1991 | Griffith |
| 5,078,140 A | 1/1992 | Kwoh |
| 5,078,142 A | 1/1992 | Siczek et al. |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,154,179 A | 10/1992 | Ratner |
| 5,160,337 A | 11/1992 | Cosman |
| 5,161,536 A | 11/1992 | Vilkomerson et al. |
| 5,172,115 A | 12/1992 | Kerth et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,189,690 A | 2/1993 | Samuel |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,229,935 A | 7/1993 | Yamagishi et al. |
| 5,230,338 A | 7/1993 | Allen et al. |
| 5,230,623 A | 7/1993 | Guthrie et al. |
| 5,233,990 A | 8/1993 | Barnea |
| 5,235,927 A | 8/1993 | Singh et al. |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,629 A | 11/1993 | Kitney et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,276,927 A | 1/1994 | Day |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Müller et al. |
| 5,368,030 A | 11/1994 | Zinreich et al. |
| 5,369,678 A | 11/1994 | Chiu et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,442,674 A | 8/1995 | Picard et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |

(56) References Cited

U.S. PATENT DOCUMENTS

| | | |
|---|---|---|
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,497,008 A | 3/1996 | Kumakhov |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,551,431 A | 9/1996 | Wells, III et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,360 A | 7/1997 | Bani-Hashemi et al. |
| 5,647,361 A | 7/1997 | Damadian |
| 5,651,047 A | 7/1997 | Moorman et al. |
| 5,662,111 A | 9/1997 | Cosman |
| 5,664,001 A | 9/1997 | Tachibana et al. |
| 5,671,265 A | 9/1997 | Andress |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,106 A * | 11/1997 | Bani-Hashemi et al. ...... 600/425 |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A * | 3/1998 | Darrow et al. ............... 600/407 |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,812,629 A | 9/1998 | Clauser |
| 5,820,553 A | 10/1998 | Hughes |
| 5,823,192 A | 10/1998 | Kalend et al. |
| 5,823,958 A | 10/1998 | Truppe |
| 5,827,187 A | 10/1998 | Wang et al. |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |

(56) References Cited

U.S. PATENT DOCUMENTS

| | | | |
|---|---|---|---|
| 5,868,674 A | 2/1999 | Glowinski et al. | |
| 5,868,675 A | 2/1999 | Henrion et al. | |
| 5,871,445 A | 2/1999 | Bucholz | |
| 5,871,455 A | 2/1999 | Ueno | |
| 5,871,487 A | 2/1999 | Warner et al. | |
| 5,873,822 A | 2/1999 | Ferre et al. | |
| 5,882,304 A | 3/1999 | Ehnholm et al. | |
| 5,884,410 A | 3/1999 | Prinz | |
| 5,889,834 A | 3/1999 | Vilsmeier et al. | |
| 5,891,034 A | 4/1999 | Bucholz | |
| 5,891,157 A | 4/1999 | Day et al. | |
| 5,904,691 A | 5/1999 | Barnett et al. | |
| 5,907,395 A | 5/1999 | Schulz et al. | |
| 5,913,820 A | 6/1999 | Bladen et al. | |
| 5,920,395 A | 7/1999 | Schulz | |
| 5,921,992 A | 7/1999 | Costales et al. | |
| 5,923,727 A | 7/1999 | Navab | |
| 5,928,248 A | 7/1999 | Acker | |
| 5,938,603 A | 8/1999 | Ponzi | |
| 5,938,694 A | 8/1999 | Jaraczewski et al. | |
| 5,947,980 A | 9/1999 | Jensen et al. | |
| 5,947,981 A | 9/1999 | Cosman | |
| 5,950,629 A | 9/1999 | Taylor et al. | |
| 5,951,475 A | 9/1999 | Gueziec et al. | |
| 5,951,571 A | 9/1999 | Audette | |
| 5,954,647 A | 9/1999 | Bova et al. | |
| 5,957,844 A | 9/1999 | Dekel et al. | |
| 5,964,796 A | 10/1999 | Imran | |
| 5,967,980 A | 10/1999 | Ferre et al. | |
| 5,967,982 A | 10/1999 | Barnett | |
| 5,968,047 A | 10/1999 | Reed | |
| 5,971,997 A | 10/1999 | Guthrie et al. | |
| 5,976,156 A | 11/1999 | Taylor et al. | |
| 5,980,535 A | 11/1999 | Barnett et al. | |
| 5,983,126 A | 11/1999 | Wittkampf | |
| 5,987,349 A | 11/1999 | Schulz | |
| 5,987,960 A | 11/1999 | Messner et al. | |
| 5,999,837 A | 12/1999 | Messner et al. | |
| 5,999,840 A | 12/1999 | Grimson et al. | |
| 6,001,130 A | 12/1999 | Bryan et al. | |
| 6,006,126 A * | 12/1999 | Cosman | 600/426 |
| 6,006,127 A | 12/1999 | Van Der Brug et al. | |
| 6,013,087 A | 1/2000 | Adams et al. | |
| 6,014,580 A | 1/2000 | Blume et al. | |
| 6,016,439 A | 1/2000 | Acker | |
| 6,019,725 A | 2/2000 | Vesely et al. | |
| 6,024,695 A | 2/2000 | Taylor et al. | |
| 6,050,724 A * | 4/2000 | Schmitz et al. | 378/205 |
| 6,059,718 A | 5/2000 | Taniguchi et al. | |
| 6,061,587 A | 5/2000 | Kucharczyk et al. | |
| 6,063,022 A | 5/2000 | Ben-Haim | |
| 6,071,288 A | 6/2000 | Carol et al. | |
| 6,073,043 A | 6/2000 | Schneider | |
| 6,076,008 A | 6/2000 | Bucholz | |
| 6,094,474 A | 7/2000 | Vezina | |
| 6,096,050 A | 8/2000 | Audette | |
| 6,104,944 A | 8/2000 | Martinelli | |
| 6,118,845 A | 9/2000 | Simon et al. | |
| 6,122,538 A | 9/2000 | Sliwa, Jr. et al. | |
| 6,122,541 A | 9/2000 | Cosman et al. | |
| 6,131,396 A | 10/2000 | Duerr et al. | |
| 6,139,183 A | 10/2000 | Graumann | |
| 6,147,480 A | 11/2000 | Osadchy et al. | |
| 6,149,592 A | 11/2000 | Yanof et al. | |
| 6,156,067 A | 12/2000 | Bryan et al. | |
| 6,161,032 A | 12/2000 | Acker | |
| 6,165,181 A | 12/2000 | Heilbrun et al. | |
| 6,167,296 A | 12/2000 | Shahidi | |
| 6,167,445 A | 12/2000 | Gai et al. | |
| 6,172,499 B1 | 1/2001 | Ashe | |
| 6,175,756 B1 | 1/2001 | Ferre et al. | |
| 6,178,345 B1 | 1/2001 | Vilsmeier et al. | |
| 6,194,639 B1 | 2/2001 | Botella et al. | |
| 6,201,387 B1 | 3/2001 | Govari | |
| 6,203,497 B1 | 3/2001 | Dekel et al. | |
| 6,211,666 B1 | 4/2001 | Acker | |
| 6,223,067 B1 | 4/2001 | Vilsmeier | |
| 6,233,476 B1 | 5/2001 | Strommer et al. | |
| 6,245,027 B1 * | 6/2001 | Alperin | 600/561 |
| 6,246,231 B1 | 6/2001 | Ashe | |
| 6,249,754 B1 | 6/2001 | Neul et al. | |
| 6,259,942 B1 | 7/2001 | Westermann et al. | |
| 6,273,896 B1 | 8/2001 | Franck et al. | |
| 6,285,902 B1 | 9/2001 | Kienzle, III et al. | |
| 6,298,262 B1 | 10/2001 | Franck et al. | |
| 6,314,310 B1 | 11/2001 | Ben-Haim et al. | |
| 6,332,089 B1 | 12/2001 | Acker et al. | |
| 6,341,231 B1 | 1/2002 | Ferre et al. | |
| 6,351,659 B1 | 2/2002 | Vilsmeier | |
| 6,356,617 B1 | 3/2002 | Besch et al. | |
| 6,379,042 B1 * | 4/2002 | Polkus et al. | 378/205 |
| 6,381,485 B1 * | 4/2002 | Hunter et al. | 600/407 |
| 6,424,856 B1 | 7/2002 | Vilsmeier et al. | |
| 6,427,314 B1 | 8/2002 | Acker | |
| 6,428,547 B1 | 8/2002 | Vilsmeier et al. | |
| 6,434,415 B1 | 8/2002 | Foley et al. | |
| 6,437,567 B1 | 8/2002 | Schenck et al. | |
| 6,445,943 B1 | 9/2002 | Ferre et al. | |
| 6,463,318 B2 | 10/2002 | Prince | |
| 6,470,207 B1 | 10/2002 | Simon et al. | |
| 6,473,635 B1 * | 10/2002 | Rasche | 600/428 |
| 6,474,341 B1 | 11/2002 | Hunter et al. | |
| 6,478,802 B2 | 11/2002 | Kienzle, III et al. | |
| 6,484,049 B1 | 11/2002 | Seeley et al. | |
| 6,490,475 B1 | 12/2002 | Seeley et al. | |
| 6,491,647 B1 | 12/2002 | Bridger et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,516,046 B1 | 2/2003 | Fröhlich et al. | |
| 6,527,443 B1 | 3/2003 | Vilsmeier et al. | |
| 6,551,325 B2 | 4/2003 | Neubauer et al. | |
| 6,584,174 B2 * | 6/2003 | Schubert et al. | 378/165 |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,669,635 B2 | 12/2003 | Kessman et al. | |
| 6,675,037 B1 | 1/2004 | Tsekos | |
| 6,690,965 B1 * | 2/2004 | Riaziat et al. | 600/428 |
| 6,694,162 B2 | 2/2004 | Hartlep | |
| 6,701,179 B1 | 3/2004 | Martinelli et al. | |
| 6,718,055 B1 * | 4/2004 | Suri | 382/128 |
| 6,990,368 B2 * | 1/2006 | Simon et al. | 600/425 |
| 7,228,165 B1 * | 6/2007 | Sullivan | 600/411 |
| 2001/0007918 A1 | 7/2001 | Vilsmeier et al. | |
| 2002/0065461 A1 * | 5/2002 | Cosman | 600/426 |
| 2002/0095081 A1 | 7/2002 | Vilsmeier | |
| 2004/0024309 A1 | 2/2004 | Ferre et al. | |

FOREIGN PATENT DOCUMENTS

| | | |
|---|---|---|
| DE | 35 08730 | 3/1985 |
| DE | 3508730 | 9/1986 |
| DE | 37 17 871 | 5/1987 |
| DE | 38 38011 | 11/1988 |
| DE | 3717871 | 12/1988 |
| DE | 3831278 | 3/1989 |
| DE | 3838011 | 7/1989 |
| DE | 3904595 | 4/1990 |
| DE | 3902249 | 8/1990 |
| DE | 42 13 426 | 4/1992 |
| DE | 42 25 112 | 7/1992 |
| DE | 4225112 | 12/1993 |
| DE | 4233978 | 4/1994 |
| DE | 4432890 | 3/1996 |
| DE | 197 15 202 | 4/1997 |
| DE | 197 47 427 | 10/1997 |
| DE | 197 51 761 | 11/1997 |
| DE | 198 32 296 | 7/1998 |
| DE | 19829230 | 3/2000 |
| DE | 10085137 | 11/2002 |
| EP | 0018166 | 10/1980 |
| EP | 0 062 941 | 3/1982 |
| EP | 0 119 660 | 9/1984 |

(56) References Cited

FOREIGN PATENT DOCUMENTS

| | | |
|---|---|---|
| EP | 0 155 857 | 1/1985 |
| EP | 0155857 A2 | 9/1985 |
| EP | 0319 844 A1 | 1/1988 |
| EP | 0 326 768 | 12/1988 |
| EP | 0419729 A1 | 9/1989 |
| EP | 0350996 A1 | 1/1990 |
| EP | 0359773 | 3/1990 |
| EP | 0651968 A1 | 8/1990 |
| EP | 0 427 358 | 10/1990 |
| EP | 0 456 103 | 5/1991 |
| EP | 0427358 | 5/1991 |
| EP | 0456103 | 11/1991 |
| EP | 0501993 | 9/1992 |
| EP | 0581704 B1 | 7/1993 |
| EP | 0655138 B1 | 8/1993 |
| EP | 0894473 A2 | 1/1995 |
| EP | 0469966 | 8/1995 |
| EP | 0 908 146 | 10/1998 |
| EP | 0 930 046 | 10/1998 |
| EP | 0908146 | 4/1999 |
| FR | 2417970 | 9/1979 |
| FR | 2 618 211 | 7/1987 |
| GB | 2 094 590 | 2/1982 |
| GB | 2094590 | 9/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 6/1998 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/00702 | 1/1992 |
| WO | WO 92/03090 | 3/1992 |
| WO | WO 92/06645 | 4/1992 |
| WO | WO 94/04938 | 3/1994 |
| WO | WO 94/06352 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/49453 | 6/1997 |
| WO | WO 97/36192 | 10/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/38449 | 8/1999 |
| WO | WO 99/60939 | 12/1999 |
| WO | WO 00/00086 | 1/2000 |
| WO | WO 01/30437 A1 | 5/2001 |

OTHER PUBLICATIONS

Oung et al., Real Time Motion Detection in Digital Subtraction Angiography, in Proceedings of the International Symposium on Medical Images and Icons, A. Deurinckx, M. H. Loew, J. M. S Prewitt (eds.), IEEE Computer Society Press, Silver Spring, RI, 1984, pp. 336-339.*

Burbank et al., Effect of Volume and Rate of Contrast Medium Injection on Intravenous Digital Subtraction Angiographic Contrast Medium Curves, JACC vol. 4, No. 2, Aug. 1984:308-15.*

Adams et al., "Orientation Aid for Head and Neck Surgeons," Innov. Tech. Biol. Med., vol. 13, No. 4, 1992, pp. 409-424.

Afshar, F. et al., A Three-Dimensional Reconstruction of the Human Brain Stem, Journal of Neurosurgery, vol. 57, No. 3, pp. 491-495 (Oct. 1982).

Awwad, E. et al., MRI Imaging of Lumber Juxtaarticular Cysts, Journal of Computer Assisted Tomography, pp. 415-417, vol. 14, No. 3 (May 1990).

Bajcsy, et al., Computerized Anatomy Atlas of the Human Brain, NCGA '81 Conference Proceedings, Second Annual Conference & Exhibition, Baltimore, MD, pp. 435-441 (Jun. 1981).

Barrick et al., Prophylactic Intramedullary Fixation of the Tibia for Stress Fracture in a Professional Athlete, Journal of Orthopaedic Trauma, vol. 6, No. 2, pp. 241-244 (1992).

Barrick et al., Technical Difficulties with the Brooker-Wills Nail in Acute Fractures of the Femur, Journal of Orthopaedic Trauma, vol. 6, No. 2, pp. 144-150 (1990).

Barrick, E. F., Journal of Orthopaedic Trauma: Distal Locking Screw Insertion Using a Cannulated Drill Bit: Technical Note, Raven Press, vol. 7, No. 3, pp. 248-251 (1993).

Batnitzky, S., et al., Three-Dimensional Computer Reconstructions of Brain Lesions from Surface Contours Provided by Computed Tomography: A Prospectus, Neurosurgery, vol. 11, No. 1, Part 1, pp. 73-84 (1982).

Benzel et al., "Magnetic Source Imaging: a Review of the Magnes System of Biomagnetic Technologies Incorporated," Neurosurgery, vol. 33, No. 2 (Aug. 1993), pp. 252-259.

Birg, W. et al., A Computer Programme System for Stereotactic Neurosurgery, Acta Neurochirurgica, Suppl. 24, pp. 99-108 (1977).

Boethius J. et al, Stereotactic Biopsies and Computer Tomography in Gliomas, Acta Neurochirurgica, vol. 49, pp. 223-232 (1978).

Boethius, J. et al., Stereotaxic Computerized Tomography With a GE 8800 Scanner, J. Neurosurg., vol. 52, pp. 794-800 (Jun. 1980).

Bouazza-Marouf et al., Robotic-Assisted Internal Fixation of Femoral Fractures, IMECHE, pp. 51-58 (1995).

Brack, C. et al., Accurate X-ray Based Navigation in Computer-Assisted Orthopedic Surgery, CAR '98, pp. 716-722.

Brack, C., et al., Towards Accurate X-Ray Camera Calibration in Computer-Assisted Robotic Surgery, CAR '96 Computer-Assisted Radiology, Proceedings of the International Symposium on Computer and Communication Systems for Image Guided Diagnosis and Therapy, Paris, pp. 721-728 (Jun. 1996).

Brunie, L. et al., Pre-and Intra-Irradiation Multimodal Image Registration: Principles and First Experiments, Radiotherapy and Oncology 29, pp. 244-252 (1993).

Bryan, "Bryan Cervical Disc System Single Level Surgical Technique", Spinal Dynamics, 2002, pp. 1-33.

Bucholz, R. et al., A Comparison of Sonic Digitizers Versus Light Emitting Diode-Based Localization, Interactive Image-Guided Neurosurgery, Chapter 16, pp. 179-200.

Bucholz, R. et al., Image-Guided Surgical Techniques for Infections and the Trauma of the Central Nervous System, Neurosurgery Clinics of North America, vol. 7, No. 2, pp. 187-200 (Apr. 1996).

Bucholz, R. et al., The Correction of Stereotactic Inaccuracy Caused by Brain Shift Using an Intraoperative Ultrasound Device, CVRMed-MRCAS '97, First Joint Conference, Computer Vision, Virtual Reality and Robotics in Medicine and Medical Robotics and Computer-Assisted Surgery, pp. 459-466 (Mar. 19-22, 1997).

Bucholz, R. et al., Variables Affecting the Accuracy of Sterotactic Localization Using Computerized Tomography, Journal of Neurosurgery, vol. 79, pp. 667-673 (Nov. 1993).

Castleman, K. et al., Stereometric Ranging, Chapter 17: Three-Dimensional Image Processing, Digital Image Processing, pp. 364-369 (1979).

Champleboux, G., et al., Accurate Calibration of Cameras and Range Imaging Sensors: The NPBS Method, Proceedings 1992 IEEE International Conference on Robotics and Automation, pp. 1552-1557 (May 12-14, 1992).

Champleboux, G., Utilisation de Fonctions Splines pour la Mise au Point d'Un Capteur Tridimensionnel sans Contact (Jul. 1991).

Cinquin, P., et al, Computer-Assisted Medical Interventions, pp. 63-65 (Sep. 1989).

(56) References Cited

OTHER PUBLICATIONS

Cinquin, P., et al., Computer-Assisted Medical Interventions, IEEE Engineering in Medicine and Biology, pp. 254-263 (May/Jun. 1995).
Clarysse, P., et al., A Computer-Assisted System for 3-D Frameless Localization in Stereotaxic MRI, IEEE Transactions on Medical Imaging, vol. 10., No. 4, pp. 523-529 (1991).
Colchester, A. et al., Information Processing in Medical Imaging, 12.sup.th International Conference, IPMI, Lecture Notes in Computer Science, pp. 135-141 (1991).
Curry, Thomas S. III, M.D., et al., Christensen's Physics of Diagnostic Radiology, 4th Edition, 1990.
Davatzikos, C. et al., Image Registration Based on Boundary Mapping, Thesis (Johns Hopkins University), pp. 1-30 (1995).
Feldmar, J. et al., 3D-2D Projective Registration of Free-Form Curves and Surfaces, Rapport de recherche (Inria Sophia Antipolis), pp. 1-44 (1994).
Foley, J. D., et al. Fundamentals of Interactive Computer Graphics, Addison-Wesley Systems Programming Series, pp. 245-266 (1982).
Foley, K. T., et al., Image-Guided Intraoperative Spinal Localization, Intraoperative Neuroprotection, Chapter 19, pp. 325-340 (1996).
Foley, K. T., The SteathStation.TM., Three-Dimensional Image-Interactive Guidance of the Spine Surgeon, Spinal Frontiers, pp. 7-9 (Apr. 1996).
Friston, K. et al., Plastic Transformation of PET Images, Journal of Computer-Assisted Tomography, vol. 15, No. 4, pp. 634-639 (1991).
Gallen, C. et al., Intracranial Neurosurgery Guided by Functional Imaging, Surgical Neurology, vol. 42, pp. 523-530 (Dec. 1994).
Germano, "Instrumentation, Technique and Technology", Neurosurgery, vol. 37, No. 2, Aug. 1995, pp. 348-350.
Gildenberg, P. L., et al., Calculation of Stereotactic Coordinates from the Computed Tomographic Scan, CT Scan Stereotactic Coordinates, pp. 580-586 (May 1982).
Gonzalez, R. C. et al., Digital Image Fundamentals, Digital Image Processing, Second Edition, Addison-Wesley Publishing, pp. 52-54 (1987).
Gottesfeld-Brown, L. M. et al., Registration of Planar Film Radiographs with Computer Tomography, Proceedings of MMBIA, pp. 42-51 (Jun. 1996).
Gouda, K. et al., New Frame for Stereotaxic Surgery, Journal of Neurosurgery, vol. 53, pp. 256-259 (Aug. 1980).
Greitz, T. et al., Head Fixation System for Integration of Radiodiagnostic and Therapeutic Procedures, Neuroradiology, vol. 19, pp. 1-6 (1980).
Gueziec, A. P. et al., Registration of Computer Tomography Data to a Surgical Robot Using Fluoroscopy: A Feasibility Study, Computer Science/Mathematics, 6 pages (Sep. 27, 1996).
Hamadeh, A. et al., Automated 3-Dimensional Computer Tomographic and Fluoroscopic Image Registration, Computer Aided Surgery, 3:11-19 (1998).
Hamadeh, A. et al., Towards Automatic Registration Between CT and X-Ray Images: Cooperation Between 3D/2D Registration and 2D Edge Detection, TIMC-IMAG Faculte de Medecine de Grenoble, pp. 39-46 (with 2 pages of drawings) (1995).
Hamadeh, A., et al., Kinematic Study of Lumbar Spine Using Functional Radiographies and 3D/2D Registration, TIMC UMR 5525—IMAG.
Hatch, et al., "Reference-Display System for the Integration of CT Scanning and the Operating Microscope", Proceedings of the Eleventh Annual Northeast Bioengineering Conference, May, 1985, pp. 252-254.
Hatch, J. F., Reference-Display System for the Integration of CT Scanning and the Operating Microscope, A Thesis Submitted to the Thayer School of Engineering, Dartmouth College, pp. 1-189 (Oct. 1984).
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M. P. et al., Stereotactic Localization and Guidance Using a Machine Vision Technique, Stereotactic and Functional Neurosurgery, vol. 58, pp. 94-98 (Sep. 1992).
Heilbrun, M. P. Progressive Technology Applications, Neurosurgery for the Third Millenium, Chapter 15, pp. 191-198 (Oct. 1992).
Henderson, J. M., et al., An Accurate and Ergonomic Method of Registration for Image-Guided Neurosurgery, Computerized Medical Imaging and Graphics, vol. 18, No. 4, pp. 273-277 (1994).
Hoerenz, P., The Operating Microscope I. Optical Principles, Illumination Systems, and Support Systems, Journal of Microsurgery, vol. 1, pp. 364-369 (1980).
Hofstetter, R. et al., Fluoroscopy Based Surgical Navigation—Concept and Clinical Applications, Computer-Assisted Radiology and Surgery, pp. 956-960 (1997).
Horner et al., "A Comparison of CT-Stereotaxic Brain Biopsy Techniques," Investigative Radiology, Sep.-Oct. 1984, pp. 367-373.
Hounsfield, G. N., Computerized Transverse Axial Scanning (Tomography): Part I. Description of System, British Journal of Radiology, vol. 46, No. 552, pp. 1016-1022 (Dec. 1973).
Jacques, S., et al., A Computerized Microstereotactic Method to Approach, 3-Dimensionally Reconstruct, Remove and Adjuvantly Treat Small CNS Lesions, Meeting of the Amer. Soc. Stereotactic and Functional Neurosurgery, Houston, Appl. Neurophysiology, 43:176-182 (1980).
Jacques, S., et al., Computerized Three-Dimensional Stereotaxic Removal of Small Central Nervous System Lesions in Patients, J. Neurosurg., 53:816-820 (1980).
Joskowicz, L. et al., Computer-Aided Image-Guided Bone Fracture Surgery: Concept and Implementation, CAR '98, pp. 710-715.
Kelly et al., "Computer-assisted stereotaxic laser resection of intra-axial brain neoplasms," Journal of Neurosurgery, vol. 64, Mar. 1986, pp. 427-439.
Kelly, P. J., et al., Precision Resection of Intra-Axial CNS Lesions by CT-Based Stereotactic Craniotomy and Computer Monitored $CO_2$ Laser, Acta Neurochirurgica 68, pp. 1-9 (1983).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee, S. et al, Computer-Assisted Spine Surgery: A Technique for Accurate Transpedicular Screw Fixation Using CT Data and a 3-D Optical Localizer, pp. 315-322 (1995).
Lavallee, S., A New System for Computer-Assisted Neurosurgery, IEEE Engineering in Medicine & Biology Society 11.sup.th Annual International Conference, pp. 926-927 (1989).
Lavallee, S., et al. Computer-Assisted Interventionist Imaging: The Instance of Stereotactic Brain Surgery, North-Holland MEDINFO 89, Part 1, pp. 613-617 (1989).
Lavallee, S., et al., Computer-Assisted Driving of a Needle into the Brain, Proceedings of the International Symposium, CAR 89, Computer-Assisted Radiology; pp. 416-420 (1989).
Lavallee, S., et al., Image Guided Operating Robot: A Clinical Application in Stereotactic Neurosurgery, Proceedings of the 1992 IEEE International Conference on Robotics and Automation, pp. 618-624 (May 1992).
Lavallee, S., et al., Matching 3-D Smooth Surfaces with Their 2-D Projections Using 3-D Distance Maps, SPIE, vol. 1570, Genometric Methods in Computer Vision, pp. 322-336 (1991).
Lavallee, S., et al., Matching of Medical Images for Computed and Robot-Assisted Surgery, IEEE EMBS (1991).
Lavallee, S., VI Adaption de la Methodologie a Quelques Applications Cliniques, Chapitre VI, pp. 133-148.
Leavitt, D. et al., Dynamic Field Shaping to Optimize Stereotactic Radiosurgery, International Journal of Radiation Oncology, Biology, Physics, vol. 21, pp. 1247-1255 (Oct. 1990).
Leksell, L. et al., Stereotaxis and Tomography—A Technical Note, ACTA Neurochirugica, vol. 52, pp. 1-7 (1980).
Lemieux, L. et al., A Patient-to-Computed Tomography Image Registration Method Based on Digitally Reconstructed Radiographs, Med. Phys. 21 (11), pp. 1749-1760 (Nov. 1994).
Levin, D. N., et al., The Brain: Integrated Three-dimensional Display of MR and PET Images, Radiology, pp. 172:783-789 (Sep. 1989).
Mazier, B., et al., Chirurgie de la Colonne Vertebrale Assistee Par Ordinateur: Application au Vissage Pediculaire, Innov. Tech. Biol. Med., vol. 11, No. 5, pp. 559-566 (1990).

(56) References Cited

OTHER PUBLICATIONS

Mazier, B., et al., Computer-Assisted Interventionist Imaging: Application to the Vertebral Column Surgery, Annual International Conference of the IEEE Engineering in Medicine and Biology Society, vol. 12, No. 1, pp. 430-431 (1990).

Merloz, et al., "Computer Assisted Spine Surgery", Clinical Assisted Spine Surgery, No. 337, pp. 86-96.

Mundinger, F. et al., Computer-Assisted Stereotactic Brain Operations by Means Including Computerized Axial Tomography, Applied Neurophysiology, vol. 41, No. 1-4, Proceedings of the Seventh Meeting of the World Society for Stereotactic and Functional Neurosurgery (1978).

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari, C. A. et al., No. 528—Three-Dimensional Correlation of PET, CT and MRI Images, The Journal of Nuclear Medicine, vol. 28, No. 4, p. 682 (Apr. 1987).

Pelizzari, C. A., et al., Accurate Three-Dimensional Registration of CT, PET, and/or MR Images of the Brain, Journal of Computer-Assisted Tomography, vol. 13, No. 1, pp. 20-26 (Jan./Feb. 1989).

Perry, J. et al., Computed Tomography—Guided Stererotactic Surgery: Conception and Development of a New Stereotactic Methodology, Neurosurgery, vol. 7, No. 4, pp. 376-381 (Oct. 1980).

Phillips, R. et al., Image Guided Orthopaedic Surgery Design and Analysis, Trans Inst MC, vol. 17, No. 5, pp. 251-264 (1995).

Potamianos, P. et al., Manipulator Assisted Renal Treatment, Centre for Robotics, Imperial College of Science, Technology & Medicine, London, pp. 214-226 (Jul. 1993).

Potamianos, P., et al., Intra-Operative Imaging Guidance for Keyhole Surgery Methodology and Calibration, First International Symposium on Medical Robotics and Computer-Assisted Surgery, pp. 98-104 (Sep. 22-24, 1994).

Potamianos, P., et al., Intra-Operative Registration for Percutaneous Surgery, Proceedings of the Second International Symposium on Medical Robotics and Computer-Assisted Surgery—Baltimore, MD—(Nov. 1995).

"Prestige Cervical Disc System Surgical Technique", 12 pgs.

Reinhardt, H. F., et al., CT-Guided "Real Time" Stereotaxy, ACTA Neurochirurgica (1989).

Roberts, D. W., et al., A Frameless Stereotaxic Integration of Computerized Tomographic Imaging and the Operating Microscope, J. Neurosurg., vol. 65, pp. 545-549 (Oct. 1986).

Rosenbaum, A. E., et al., Computerized Tomography Guided Stereotaxis: A New Approach, Meeting of the Amer. Soc. Stereotactic and Functional Neurosurgery, Houston, Appl. Neurophysiol., 43:172-173 (1980).

Rougee, A., et al., Geometrical Calibration of X-Ray Imaging Chains for Three-Dimensional Reconstruction, Computerized Medical Imaging and Graphics, vol. 17, No. 4/5, pp. 295-300 (1993).

Sautot, "Vissage Pediculaire Assiste Par Ordinateur," Sep. 20, 1994.

Sautot, Pascal Phillipe, Computer Assisted Introduction of Screws Into Pedicles, Thesis, pp. 1-163 (Sep. 1994).

Schreiner, S., et al., Accuracy Assessment of a Clinical Biplane Fluoroscope for Three-Dimensional Measurements and Targeting, Proceedings of SPIE, Image Display, vol. 3031, pp. 160-166 (Feb. 23-25, 1997).

Schueler, B., Correction of Image Intensifier Distortion for Three-Dimensional X-ray Angiography, Proceedings of SPIE, Physics of Medical Imaging, vol. 2432, pp. 272-279 (Feb. 26-27, 1995).

Selvik, G., et al., A Roentgen Stereophotogrammetric System, Acta Radiologica Diagnosis, pp. 343-352 (1983).

Shelden, C. H., et al., Development of a Computerized Microstereotaxic Method for Localization and Removal of Minute CNS Lesions Under Direct 3-D Vision, J. Neurosurg., 52:21-27 (1980).

Simon, D., Fast and Accurate Shape-Based Registration, Carnegie Mellon University (Dec. 12, 1996).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K. et al., The Neurostation.TM.—A Highly Accurate, Minimally Invasive Solution to Frameless Stereotactic Neurosurgery, Computerized Medical Imaging and Graphics, vol. 18, No. 4, pp. 247-256 (Jul.-Aug. 1994).

Smith, K. R., et al., Computer Methods for Improved Diagnostic Image Display Applied to Stereotactic Neurosurgery, Automedical, vol. 14, pp. 371-386 (1991).

The Laitinen Stereotactic System, E2-E6.

Troccaz, J. et al., Conformal External Radiotherapy of Prostatic Carcinoma: Requirements and Experimental Results, Radiotherapy and Oncology 29, pp. 176-183 (1993).

Viant, W. J. et al., A Computer-Assisted Orthopaedic System for Distal Locking of Intramedullary Nails, Proc. of MediMEC '95, Bristol, pp. 86-91 (1995).

Watanabe, E., et al., Three-Dimensional Digitizer (Neuronavigator): New Equipment for Computed Tomography-Guided Stereotaxic Surgery, Surgical Neurology, vol. 27, No. 6, pp. 543-547 (Jun. 1987).

Watanabe, H., Neuronavigator, Igaku-no-Ayumi, vol. 137, No. 6, pp. 1-4 (May 10, 1986).

Weese, J., et al., An Approach to 2D/3D Registration of a Vertebra in 2D X-ray Fluoroscopies with 3D CT Images, First Joint Conference Computer Vision, Virtual Reality and Robotics in Medicine and Med. Robotics and Computer-Assisted Surgery, Grenoble, France, pp. 119-128 (Mar. 19-22, 1997).

Adams et al., Computer-Assisted Surgery, IEEE Computer Graphics & Applications, pp. 43-51, (May 1990).

Bergstrom et al. Stereotaxic Computed Tomography, Am. J. Roentgenol, vol. 127 pp. 167-170 (1976).

Brown, R., M.D., A Stereotactic Head Frame for Use with CT Body Scanners, Investigative Radiology © J.B. Lippincott Company, pp. 300-304 (Jul.-Aug. 1979).

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., Jr. et al, Optical localization for interactive, image-guided neurosurgery, SPIE, vol. 2164, pp. 137-145 (undated.

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Stereotaxy, Image Guided Surgery, and enhanced Reality Visualization, IEEE, pp. 430-436 (1994).

(56) References Cited

OTHER PUBLICATIONS

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Guthrie, B.L., Graphic-Interactive Cranial Surgery: The Operating Arm System, Handbook of Stereotaxy Using the CRW Apparatus, Chapter 13, pp. 193-211 (undated.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Kall, B., The Impact of Computer and lmgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Computer-Directed Stereotactic Resection of Brain Tumors, Neurologica Operative Atlas, vol. 1, No. 4, pp. 299-313 (1991).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed. Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Ng, W.S. et al., Robotic Surgery-A First-Hand Experience in Transurethral Resection of the Prostate Surgery, IEEE Eng. in Med. and Biology, pp. 120-125 (Mar. 1993).
Penn, R.D., et al., Stereotactic Surgery with Image Processing of Computerized Tomographic Scans, Neurosurgery, vol. 3, No. 2, pp. 157-163 (Sep.-Oct. 1978).
Pixsys, 3-D Digitizing Accessories, by Pixsys (marketing brochure)(undated) (2 pages).
Reinhardt, H., et al., A Computer-Assisted Device for Intraoperative CT-Correlated Localization of Brain Tumors, pp. 51-58 (1988).
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).
Reinhardt, Hans. F., Neuronavigation: A Ten-Year Review, Neurosurgery, pp. 329-341 (undated).
Simon, D.A., Accuracy Validation in Image-Guided Orthopaedic Surgery, Second Annual Intl. Symp. on Med. Rob. an Comp-Assisted surgery, MRCAS '95, pp. 185-192 (undated).
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
Thompson, et al., A System for Anatomical and Functional Mapping of the Human Thalamus, Computers and Biomedical Research, vol. 10, pp. 9-24 (1977).
Trobraugh, J.W., et al., Frameless Stereotactic Ultrasonography: Method and Applications, Computerized Medical Imaging and Graphics, vol. 18, No. 4, pp. 235-246 (1994).
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe, E., M.D., et al., Open Surgery Assisted by the Neuronavigator, a Stereotactic, Articulated, Sensitive Arm, Neurosurgery, vol. 28, No. 6, pp. 792-800 (1991).

\* cited by examiner

202

204

METHOD AND APPARATUS FOR VIRTUAL DIGITAL SUBTRACTION ANGIOGRAPHY

CROSS-REFERENCE TO RELATED APPLICATIONS

This application is a continuation of U.S. patent application Ser. No. 10/116,631 filed on Apr. 4, 2002. The disclosure of the above application is incorporated herein by reference.

FIELD OF THE INVENTION

The present invention relates generally to medical imaging systems and, more particularly, to a system that detects any change in relative position between a patient and the imaging device and corrects the image data for any such motion that occurs.

BACKGROUND OF THE INVENTION

Modern diagnostic medicine has benefited significantly from radiology. Radiation, such as x-rays, may be used to generate images of internal body structures. In general, radiation is emanated towards a patient's body and absorbed in varying amounts by tissues in the body. An x-ray image is then created based on the relative differences of detected radiation passing through the patients' body.

Digital subtraction is a well known technique for visually enhancing differences between such images. For example, digital subtraction angiography (DSA) is used to visualize vasculature by comparing two or more images of the same blood vessels before and after injection of a contrast agent. Assuming that the only change between the pre-contrast image (or "mask") and the contrast-containing image is related to the injection of the contrast agent, the "difference image" clearly outlines the vessels into which the contrast agent has flowed.

However, digital subtraction techniques assume a fixed relative position between the imaging device and the patient being imaged for any images which are being compared. If this relative position changes between the time that the initial image (the one to which all subsequent images are compared) is acquired and the time that any of the subsequent images are acquired, the difference image will not only convey changes in the anatomy of the patient, but also any "artifacts" or changes introduced by this change in relative position between the imaging device and the patient.

Therefore, it is desirable to provide a medical imaging system that addresses the patient motion artifact problem. It is envisioned that the system will directly measure the relative position between the imaging device and the patient, and then compensate the images for any motion that occurs between the time at which the initial image is acquired and the time at which any subsequent images are acquired by the imaging system.

SUMMARY OF THE INVENTION

In accordance with the present invention, a medical imaging system is provided that detects any change in relative position between the patient and the imaging device and compensates the image data for any patient motion that occurs. The medical imaging system includes: an imaging device for capturing two or more image data sets representative of a patient; a tracking subsystem for detecting patient position data that is indicative of the position of the patient and device position data that is indicative of the position of the imaging device; an image subtraction subsystem for performing a digital subtraction operation between at least two image data sets; and a motion correction subsystem configured to detect a change in the relative position between the patient and the imaging device and upon detecting a change in the relative position, compensate in at least one of the first image data set and the second image data set for the change in relative position prior to performing the digital subtraction operation. The digital subtraction image can detect the motion of a therapeutic device, motion of a therapy as it moves through the body, perfusion of a substance, contrast agents, chemical change of a substance, a drug as it attaches itself to anatomical material or interacts with diseased tissue, or any device or substance that has an image signature within one or multiple image modalities. The digital subtraction of any 3D volume such as those created by MR, CT, Isocentric C-arms, C-arms tracked to construct volumes, 3D ultrasound, etc. can now be viewed from any angle or with any cut plane. It is also important to point out that the tracking subsystem can be implemented via a number of different devices or techniques in order to correct for patient motion. Simple modeling of patient respiration or heart cycles can be used in conjunction with a tracking subsystem or solely to provide motion correction. The system could use actual signals as inputs to these models.

For a more complete understanding of the invention, reference may be had to the following specification and to the accompanying drawings.

DETAILED DESCRIPTION OF THE PREFERRED EMBODIMENTS

Figure 1:
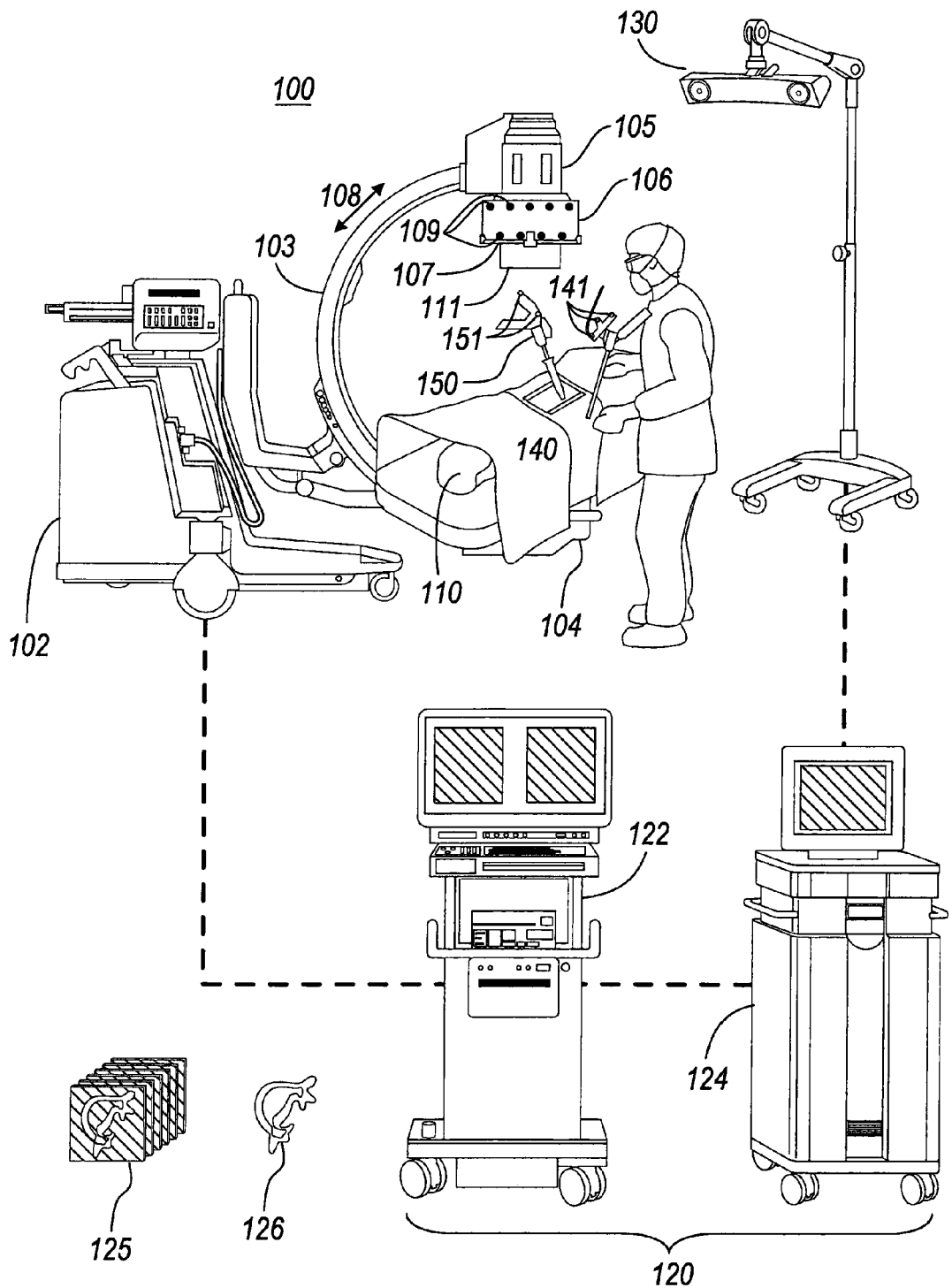
FIG. 1 is a diagram of a surgical instrument navigation system in accordance with present invention.

FIG. 1 is a diagram of an exemplary surgical instrument navigation system. The primary component of the surgical instrument navigation system is a fluoroscopic imaging device 100. The fluoroscopic imaging device 100 generally includes a C-arm 103 attached to a mobile base 102 or fixed room system. An x-ray source 104 is located at one end of the C-arm 103 and an x-ray receiving section 105 is located at the other end of the C-arm 103. In addition, the fluoroscopic imaging device 100 includes a calibration and tracking target 106 attached to the x-ray receiving section 105. As will be further described below, the calibration and tracking target 106 further includes one or more radiation sensors 107, a plurality of tracking targets 109, and a plurality of calibration markers 111. While the following description is provided by reference to an x-ray imaging device, it is readily understood that other types on imaging devices, such as a computed tomography imaging device, a magnetic resonance imaging device or an ultra-sound device, are within the scope of the present invention. It is also readily understood that two-dimensional projection images or three-dimensional volumetric images are within the scope of the present invention.

In operation, a patient 110 is positioned between the x-ray source 104 and the x-ray receiving section 105. In response to an operator's command input, x-rays emanating from source 104 pass through the patient area, including the patient 110 and the calibration and tracking target 106, and into the receiving section 105 of the imaging device. The receiving section 105 generates a two-dimensional image based on the intensities of the received x-rays. To do so, the receiving section 105 may be comprised an image intensifier that converts the x-rays to visible light and a charge coupled device (CCD) video camera that converts the visible light to digital images. Alternatively, the receiving section 105 may be a device that converts x-rays directly to digital images, thus potentially avoiding distortion introduced by first converting to visible light.

Furthermore, the C-arm 103 is capable of rotating relative to the patient 110, thereby allowing images of the patient 110 to be taken from multiple directions. For example, the physician may rotate the C-arm 103 in the direction of arrows 108 or about the long axis of the patient 110. Each of these directions of movement involves rotation about a mechanical axis of the C-arm 103. In this example, the long axis of the patient 110 is aligned with the mechanical axis of the C-arm 103. In sum, the imaging device 100 is generally operable to capture one or more sets of image data representative of the patient 110.

Resulting fluoroscopic images are then transmitted to an image processing device 120. In one embodiment, the image processing device 120 may be comprised of two computers. A control computer 122 which allows a physician to control the fundamental operation of the imaging device 100, such as setting imaging parameters, and a second computer 124 which may be used to perform more robust image processing functions. It is envisioned that either computer may provide facilities for displaying, saving, digitally manipulating, or printing a hard copy of the received images. It is further envisioned that images may be displayed to the physician through a heads-up display (not shown). It is readily understood that these computing functions may be integrated into a single computer or distributed across three or more computing devices.

An exemplary imaging device 100 is the Series 9800 Mobile Digital Imaging System manufactured by OEC Medical Systems, Inc. of Salt Lake City, Utah. It should be noted that calibration and tracking target 106 is typically not included in the Series 9800 Mobile Digital Imaging System, but otherwise this system is similar to the imaging system 100 described above. An alternative imaging device is the SIREMOBILE Iso-C System manufactured by Siemens Medical Systems, Inc. of Iselin, N.J.

Figure 2A:
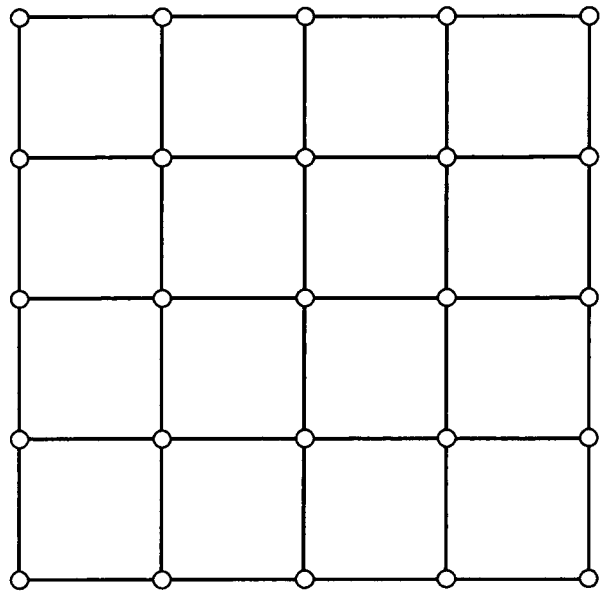
FIG. 2 is a diagram of a true and a distorted image that may be captured by the surgical navigation system.
Figure 2B:
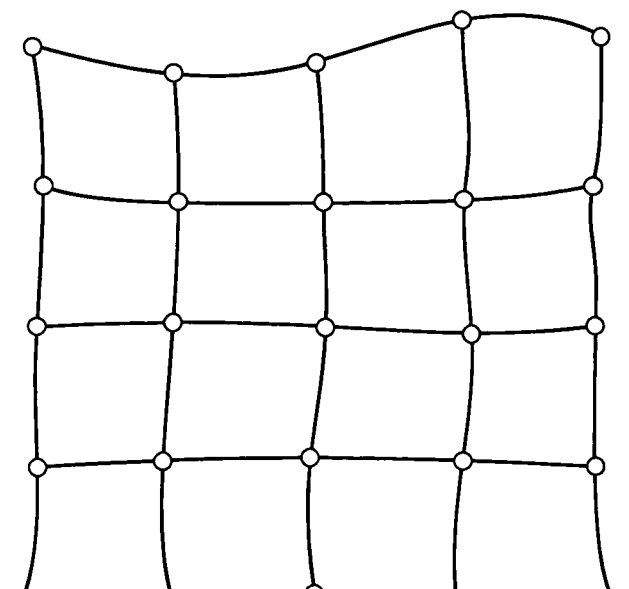

Intrinsic calibration is the process of correcting image distortion in a received image and establishing the projective transformation for that image. Raw images generated by the receiving section 105 tend to suffer from undesirable distortion caused by a number of factors, including inherent image distortion in the image intensifier and external electromagnetic fields. An example of a true and a distorted image is shown in FIG. 2. Checkerboard 202 represents the true image of a checkerboard shaped object placed in the image tracking area. The image taken by receiving section 105, however, can suffer significant distortion, as illustrated by the distorted image 204.

Figure 3A:
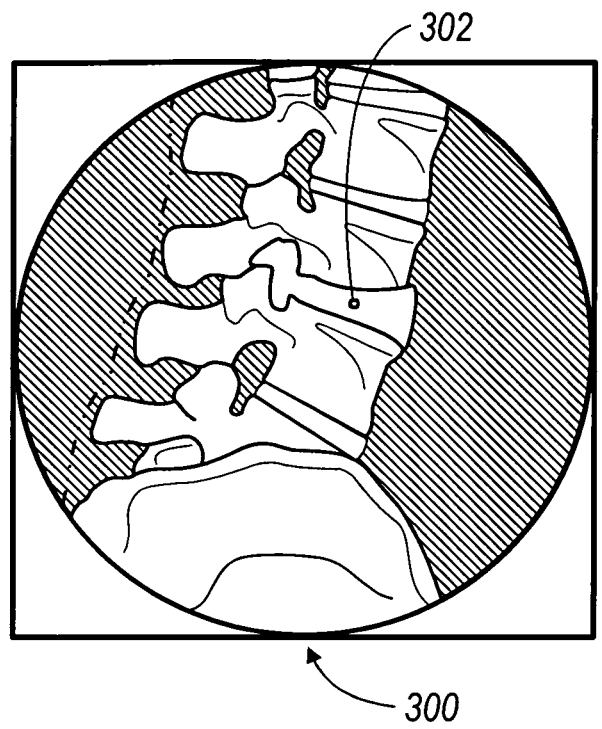
FIGS. 3A and 3B illustrates the projective transformation process employed by the surgical navigation system.
Figure 3B:
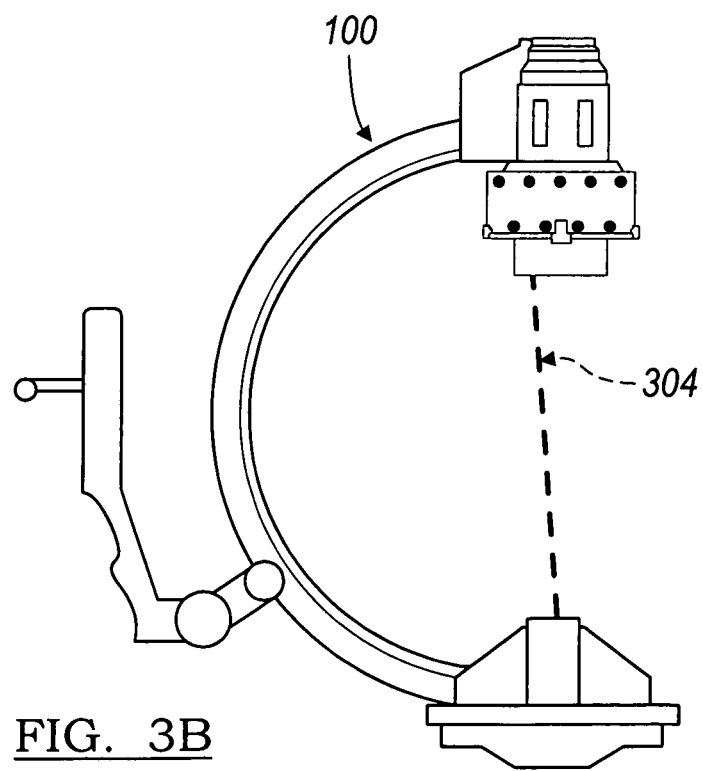

Furthermore, the image formation process is governed by a geometric projective transformation which maps lines in the fluoroscope's field of view to points in the image (i.e., within the x-ray receiving section 105). This concept is illustrated in FIGS. 3A and 3B. Image 300 (and any image generated by the fluoroscope) is composed of discrete picture elements (pixels), an example of which is labeled as 302. Every pixel within the image 300 has a corresponding three-dimensional line in the fluoroscope's field of view. For example, the line corresponding to pixel 302 is labeled as 304. The complete mapping between image pixels 302 and corresponding lines 304 governs projection of objects within the field of view into the image. The intensity value at pixel 302 is determined by the densities of the object elements (i.e., portions of a patient's anatomy, operating room table, etc.) intersected by the line 304. For the purpose of computer assisted navigational guidance, it is necessary to estimate the projective transformation which maps lines in the field of view to pixels in the image, and vice versa.

Intrinsic calibration involves placing "calibration markers" in the path of the x-ray, where a calibration marker is an object opaque or semi-opaque to x-rays. Calibration markers 111 are rigidly arranged in predetermined patterns in one or more planes in the path of the x-rays and are visible in the recorded images. Because the true relative position of the calibration markers 111 in the recorded images are known, the image processing device 120 is able to calculate an amount of distortion at each pixel 302 in the image (where a pixel is a single point in the image). Accordingly, the image processing device 120 can digitally compensate for the distortion in the image and generate a distortion-free, or at least a distortion improved image. Alternatively, distortion may be left in the image, and subsequent operations on the image, such as superimposing an iconic representation of a surgical instrument on the image (described in more detail below), may be distorted to match the image distortion determined by the calibration markers.

Since the position of the calibration markers 111 are known with respect to the tracking targets 109 and ultimately with respect to a tracking sensor, the calibration markers 111 can also be used to estimate the geometric perspective transformation. A more detailed explanation of methods for performing intrinsic calibration is described in the following references B. Schuele et al., "Correction of Image Intensifier Distortion for Three-Dimensional Reconstruction," presented at SPIE Medical Imaging 1995, San Diego, Calif., 1995 and G. Champleboux et al., "Accurate Calibration of Cameras and Range Imaging Sensors: the NPBS Method," Proceedings of the 1992 IEEE International Conference on Robotics and Automation, Nice, France, May 1992, and U.S. Pat. No. 6,118,845, issued Sep. 12, 2000 by the present assignee, the contents of which are hereby incorporated by reference.

The surgical instrument navigation system further includes a tracking subsystem. The tracking subsystem is generally comprised of a non-contact position location sensor, numerous tracking targets embedded in different system components and accompanying computational software implemented in the image processing device 120. In a preferred embodiment, the tracking subsystem employs a real-time infrared tracking sensor 130. Although an infrared-based tracking subsystem (either passive or active) is presently preferred, it is envisioned that other well known types of positional location devices may be used to implement the tracking subsystem. For example, positional location devices based on mechanical arms, robotics, radio wave, magnetic fields, fiber optic, or sonic emissions are also within the scope of the present invention.

The tracking sensor 130 detects the presence and location of a surgical instrument 140. To do so, the specially constructed surgical instrument 140 is embedded with tracking targets 141, such as infrared reflectors or emitters. Because the relative spatial locations of the tracking targets 141 on the surgical instrument 140 are known a priori, the tracking subsystem is able to determine the location of the surgical instrument 140 in three-dimensional space using well known mathematical transformations.

During an operation, a dynamic reference frame marker 150 is attached in a fixed position relative to the portion of the patient 110 to be operated on. For example, when inserting a screw into the spine of the patient 110, the dynamic reference frame marker 150 may be physically attached to a portion of the spine of the patient 110. The reference frame marker 150 is similarly embedded with tracking targets 151, such as infrared reflectors or emitters. In this way, the tracking sensor 130 is also able to determine the location of reference frame marker 150 in three-dimensional space.

Consequently, the surgical instrument 140 can be accurately located in three dimensional space relative to the reference frame marker 150 and thus can be located relative to the patient's anatomy. The determination of the three-dimensional position of an object, such as the reference frame marker, relative to a patient is known in the art, and is discussed, for example, in the following references, each of which are hereby incorporated by reference: PCT Publication WO 96/11624 to Bucholz et al., published Apr. 25, 1996; U.S. Pat. No. 5,384,454 to Bucholz; U.S. Pat. No. 5,851,183 to Bucholz; and U.S. Pat. No. 5,871,445 to Bucholz.

Lastly, the calibration and tracking target 106 also includes tracking targets 109, such as infrared reflectors or emitters. In a similar manner, the tracking sensor 130 detects the presence and location of the tracking targets 109. Since the calibration and tracking target 106 is in a fixed position relative to the x-ray receiving section 105, the image processing device 120 can further determine the three-dimensional position of the x-ray receiving section 105 relative to the surgical instrument 140 and/or the dynamic reference frame 150 (and thus the patient).

In one embodiment, the tracking sensor 130 determines the position of the x-ray receiving section 105 at each point in time that it captures image data. In an alternative embodiment, position data for the x-ray receiving section 105 is reported by a mechanical localizer associated with the imaging device 100. The mechanical localizer is operable to report position data for the x-ray receiving section 105 relative to a baseline position. In operation, the tracking sensor 130 may be used to determine the baseline position of the x-ray receiving section 105 relative to the either the surgical instrument 140 and/or the dynamic reference frame 150. Alternatively, you may simply touch the surgical instrument 140 to various reference points on the x-ray receiving section 105. Thereafter, as position of the x-ray receiving section 105 changes over time, its position is reported by the mechanical localizer. In other words, by first determining the baseline location, subsequent movement and location of imaging device 100 can be determined by monitoring the drive or movement mechanism surgical localizer of the imaging device 100. The image processing device 120 can then determine the position of the x-ray receiving device 105 relative to either the surgical instrument 140 and/or the dynamic reference frame 150.

In operation, the enhanced surgical navigation system assists physicians performing surgery by displaying real-time or pre-acquired images, such as fluoroscopic x-ray images, of the patient 110 on a display associated with image processing device 120 that is visible to the surgeon. Representations of surgical instruments 140 are overlaid on pre-acquired fluoroscopic images of the patient 110 based on the position of the instruments 140 as determined by the tracking sensor 130. In this manner, the surgeon is able to see the location of the instrument 140 relative to the patient's anatomy, without the need to acquire real-time fluoroscopic images, thereby greatly reducing radiation exposure to the patient and to the surgical team.

Figure 4:
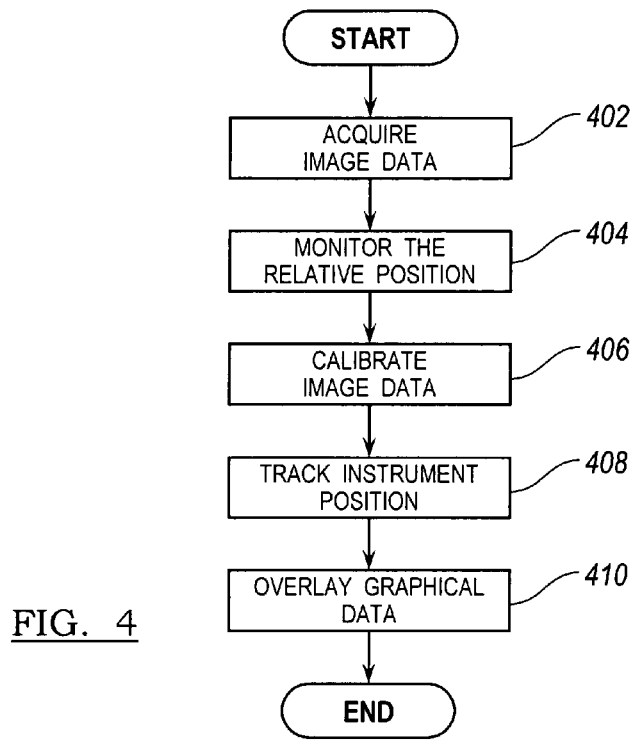
FIG. 4 is a flowchart depicting the operation of the enhanced surgical navigation system of the present invention.

FIG. 4 is a flowchart depicting the operation of the surgical navigation system. The physician begins by acquiring one or more fluoroscopic x-ray images 125 of the patient 110 using the imaging device 100 as shown at 402. Radiation sensors 107 embedded in the calibration and tracking target 106 may be used to detect the presence of radiation. The image processing device 120 uses input from the radiation sensors 107 to determine the beginning and end of a radiation cycle. Alternatively, the operator may manually indicate the beginning and end of a radiation cycle or a signal may be sent from the imaging device.

For a fluoroscopic x-ray image to be useable for navigational guidance, the imaging device 100 must be stationary with respect to the patient 110 during image acquisition. If the C-arm 103 or the patient 110 is moving during image acquisition, the position of the imaging device will not be accurately determined relative to the patient's reference frame. Thus, it is important that the recorded position of imaging device 100 reflects its true position at the time of image acquisition.

During the image acquisition process, the image processing device 120 continuously examines the relative position between the patient 110 and the imaging device 100 as shown at 404. If the imaging device 100 moves during the image acquisition process, or if the imaging device 100 moves after image acquisition but before its position is recorded, calibration measurements will be erroneous, thereby resulting in incorrect graphical overlays. To prevent this type of erroneous image, image data may be discarded if the patient 110 moves relative to the imaging device 100 during the image acquisition process.

At the end of the radiation cycle, the image processing device 120 retrieves the acquired image data as well as positional data for the imaging device 100 and the dynamic reference frame 150. The image processing device 120 subsequently calibrates the acquired image to learn its projective transformation and optionally to correct distortion in the image at 406. Calibrated image data along with corresponding positional data is then stored. These processing steps are repeated for each image that is acquired.

During surgery, the tracking sensor 130 detects the position of surgical instrument 140 relative to the dynamic reference frame 150, and hence relative to the patient 110 at 408. The image processing device 120 dynamically computes, in real-time, the projection of instrument 140 into each fluoroscopic image as the instrument 140 is moved by the physician. A graphical representation of instrument 140 may then be overlaid on the fluoroscopic images at 410. The graphical representation of instrument 140 is an iconic representation of where the actual surgical instrument 140 would appear within the acquired fluoroscopic x-ray image as if the imaging device 100 was continuously acquiring new images from the same view as the original image. There is no theoretical limit to the number of fluoroscopic images on which the graphical representations of instrument may be simultaneously overlaid.

Figure 5:
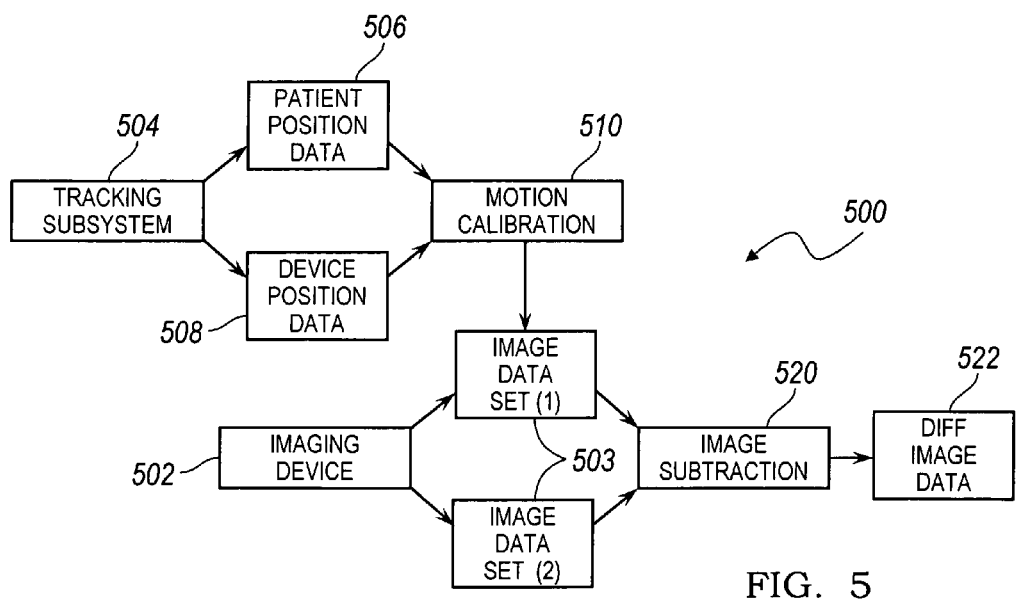
FIG. 5 is a block diagram of an enhanced surgical instrument navigation system in accordance with the present invention.

In accordance with the present invention, the surgical instrument navigation system described above has been enhanced to detect any change in relative position between the patient 110 and the imaging device 100, and compensate image data for any such patient motion. Referring to FIG. 5, the enhanced surgical navigation system 500 includes an imaging device 502 and a tracking subsystem 504. As described above, the imaging device 502 is operable to capture one or more image data sets representative of a patient; whereas the tracking subsystem 504 is operable to determine patient position data 506 indicative of the position of the patient as well as device position data 508 indicative of the position of the imaging device.

The enhanced surgical instrument navigation system 500 further includes a motion correction subsystem 510 and an image subtraction subsystem 520. The image subtraction subsystem 520 is adapted to receive two image data sets 503 from the imaging device 502. The image subtraction subsystem 520 is then operable to perform a digital subtraction operation between the two image data sets, thereby generating resulting image data 522 indicative of the differences between the two image data sets. Further explanation of exemplary digital subtraction techniques is described in Christensen's Physics of Diagnostic Radiology by Thomas S. Curry, III, James E. Dowdey, and Robert C. Murry, Jr., $4^{th}$ Ed. 1990, the contents of which are hereby incorporated by reference. It is readily understood that various well known digital subtraction techniques are within the scope of the present invention. It is further understood that other comparison techniques for assessing image data acquired at different points in time are also within the scope of the present invention. Any sort of image analysis or comparison can be applied to such a technique as segmentation, volume rendering, or shape analysis to a brain structure such as the hippocampus or tumor growth. One such technique for shape analysis is described in U.S. patent application Ser. No. 09/326,657 Method and Apparatus for Automatic Shape Characterization and U.S. Pat. No. 6,226,418 which are specifications are here included.

Figure 7:
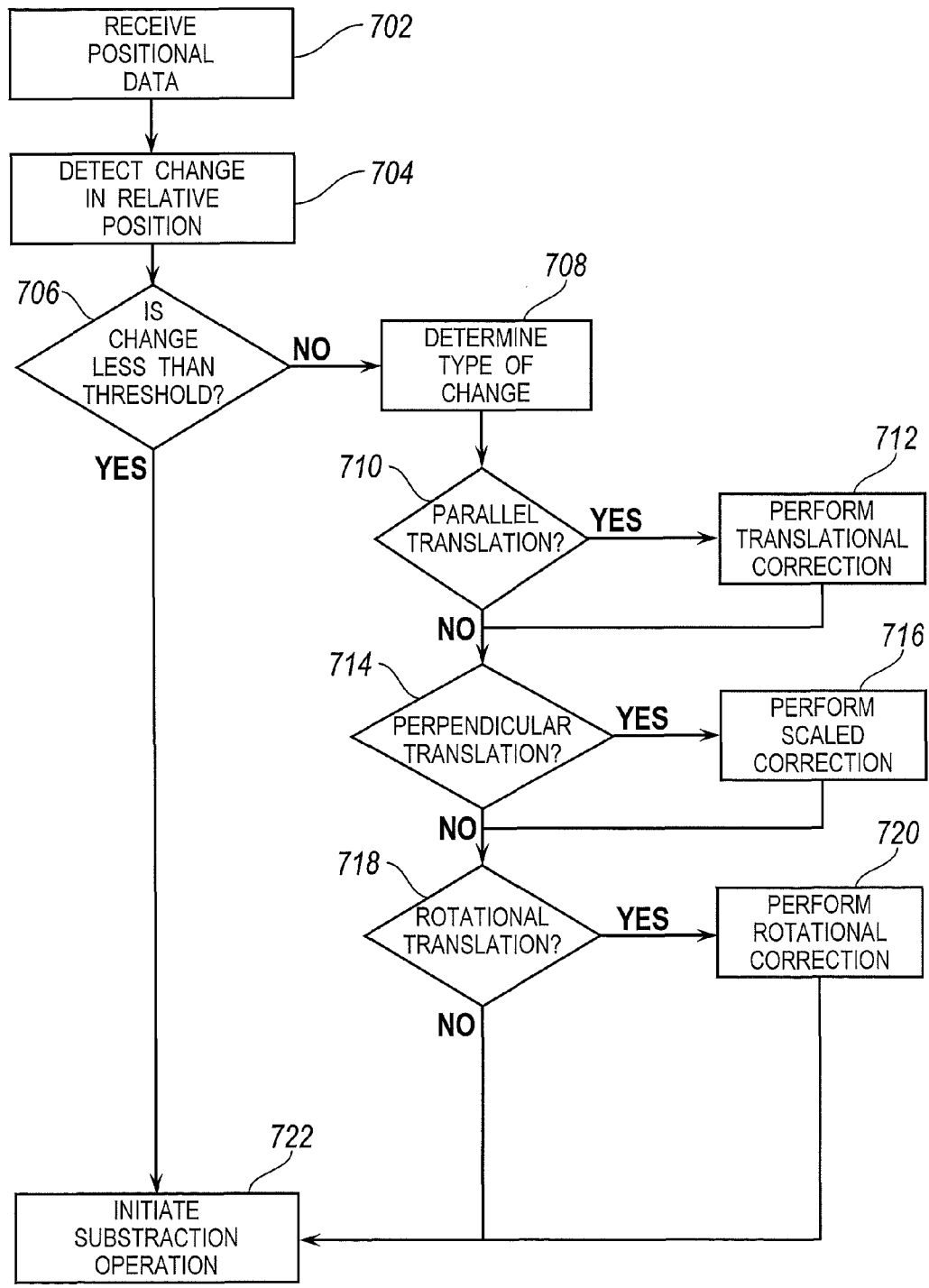
FIG. 7 is a flowchart depicting the operation of the motion correction subsystem in accordance with the present invention.

Prior to performing a digital subtraction operation, the motion correction subsystem 510 may be used to detect any patient motion that occurs between the times at which the image data is acquired. Referring to FIG. 7, the motion correction subsystem 510 is adapted to receive the patient position data 506 and device position data 508 corresponding to each of the two image data sets 503 as shown at 702. The motion correction subsystem 510 is then operable to detect any change in the relative position between the patient and the imaging device as shown at 704.

In one embodiment, the detection of patient motion merely serves as a triggering event for the operation of the enhanced surgical navigation system 500. When no change occurs in the relative position of the patient, a digital subtraction operation may simply be performed by the image subtraction subsystem 520. Alternatively, the digital subtraction operation may be performed when the measured change in relative position is less than a predetermined threshold value in block 706 that is indicative of a maximum acceptable change in the relative position between the patient and the imaging device. On the other hand, when a unacceptable amount of patient motion is detected, the motion correction subsystem 510 may initiate an alternate operation, such as providing an operator alarm.

In another embodiment, the motion correction subsystem 510 may measure the change in relative position between the patient and the imaging device over time. When the measured change in relative position is less than the predetermined threshold value in block 706, the motion correction subsystem 510 initiates the digital subtraction operation at 722. On the other hand, when the measured change in relative position is equal to or greater than the predetermined threshold value, the motion correction subsystem 510 will apply a suitable correction to at least one of the two image data sets.

Figure 6A:
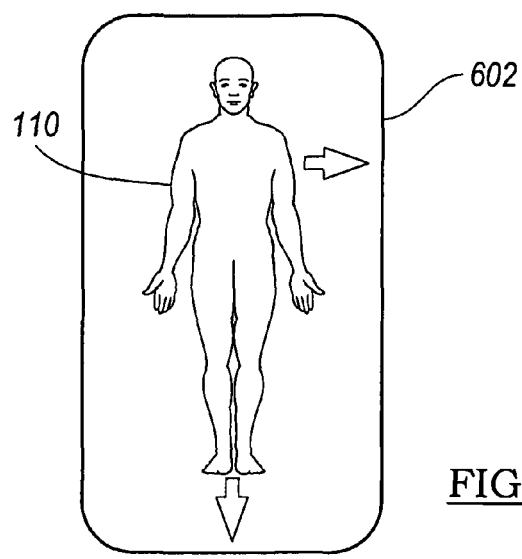
FIGS. 6A-6C illustrates the different types of changes in the relative position between the patient and the imaging device.
Figure 6B:
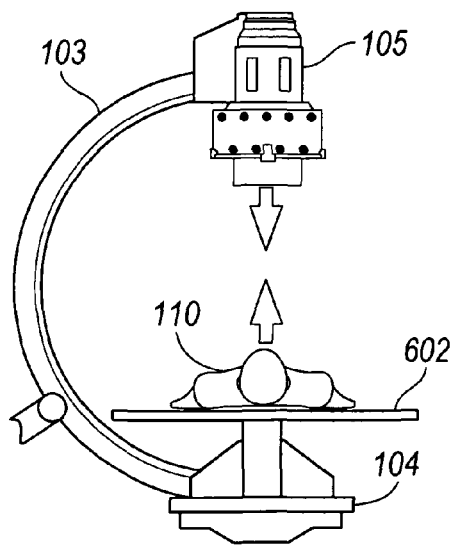

Since the suitable correction depends upon the nature of the relative motion, the motion correction subsystem 501 is operable to determine the nature of the relative motion at 708. For instance, when the relative motion (or change in relative position) is a translation that is parallel to the imaging plane 602 of the imaging device as determined in block 710, a suitable translation correction would be performed to one of the two images as shown at 712. FIG. 6A illustrates a translation that is parallel to the imaging plane 602 of the imaging device (e.g., the face of the image intensifier of a fluoroscope). When the relative motion is a translation that is perpendicular as determined in block 714 to the imaging plane 602, a change occurs in the scale or size of the imaged anatomy as shown at 716. In this case, a suitable scale correction would be performed to one of the two images. FIG. 6B illustrates a translation that is perpendicular to the imaging plane 602 of the imaging device (as represented by the top surface of operating table). Suitable image correction techniques are well known in the art.

Figure 6C:
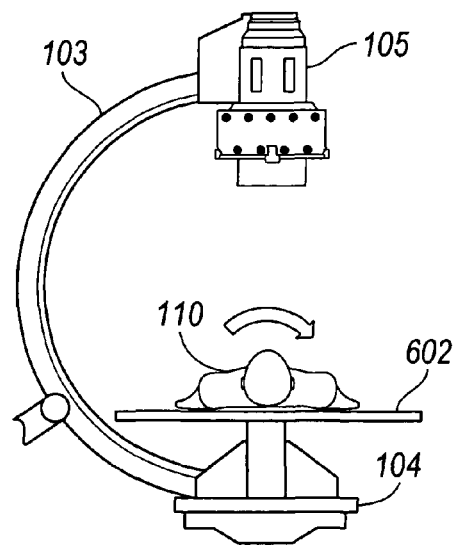

When the relative motion is a rotation of the imaging device about the patient's anatomy as determined in block 718, the ability to perform a correction depends upon the magnitude and direction of the rotation. FIG. 6C illustrates motion that is rotational to the imaging plane 602 of the imaging device. Rotations of the imaging device relative to the anatomy in a plane parallel to the image plane can be corrected by applying an appropriate in plane rotation to one of the two images. However, in the case of two-dimensional projection imaging, it is impossible to correct for arbitrary rotations without knowing the three-dimensional shape of the underlying anatomy. In some of these cases, the rotational correction may be approximated using known translation techniques. Therefore, it is envisioned that the motion correction subsystem 510 may further include a mechanism for determining when a rotational correction can be performed by a translation and then applying an appropriate rotational translation as shown at 720. It is readily understood that in the case of three-dimensional volumetric images 126, the limitation on correcting for rotations does not apply, and a complete correction can be applied to the image data.

Once an appropriate correction has been applied to either of the two image data sets, the motion correction subsystem 510 initiates a digital subtraction operation at 722. It is to be understood that only the relevant steps of the methodology are shown in FIG. 7, but that other software-implemented instructions may be needed to control and manage the overall operation of the subsystem.

In two-dimensional projection imaging, determining how to apply a correction to an image given a measurement of the relative motion between patient and the imaging device requires an additional piece of information. In particular, the intrinsic calibration parameters of the imaging device must be known to the motion correction subsystem 510.

In three-dimensional digital subtraction, it is possible to compute volume changes of the contrast media as a function of time. Once the motion correction is applied, this would be computed as the volume of the difference image above a given intensity threshold. This difference volume could be further constrained to lie within a segmented region (e.g., within a vertebral body, outside a vertebral body). Computation of other shape attributes (surface area, moments of inertia, etc.) are also possible.

It is further envisioned that the motion correction subsystem 510 may be configured to eliminate motion artifacts caused by changes in the position of the tracked surgical instrument 140. Recall that any changes in the imager's field of view will result in an enhanced region of the difference image. Typically, the motion of the surgical instrument 140 is not clinically relevant and, therefore, it would be desirable to eliminate these enhanced regions from any resulting difference image. Using the measured positions of a given instrument 140 relative to the imaging device 100, together with data for the three-dimensional shape of the instrument (e.g., from a CAD model), it is possible to compute the resulting enhanced region in the difference image. Once this region is known, it is then possible to eliminate this instrument-induced motion artifact from the image. It is to be understood that this function can be applied to either two-dimensional projection images or three-dimensional volumetric images.

While the above description is provided with reference to a surgical navigation system, it is readily understood that the broader aspects of the present invention are generally applicable to medical imaging systems where motion between the patient and the imaging device is suspected.

Moreover, it is readily understood that the present invention is applicable to different types of medical applications. One medical application of interest is vertebroplasty, in which bone cement is injected into a vertebral body of the spine via a needle that passes through the spinal pedicle. Leakage of this cement into surrounding structures can result in serious complications. Therefore, visualizing the spread of this cement over time is critical so that the clinician can ensure that the cement does not leave the vertebral body. One way to achieve this goal is by using single or multi-planar fluoroscopic imaging to view the anatomical structures as the above-mentioned cement is introduced. Unfortunately, the cement is often poorly visualized in the fluoroscopic images. Digital subtraction radiology provides a mechanism for highlighting the location of the cement by comparing a pre-cement image to one or more images acquired while the cement is being injected. Unfortunately, due to the nature of the clinical procedure, there is a moderate likelihood that the spinal anatomy will move relative to the imaging device as the cement is being injected. By applying the methods and systems of the present invention, it is possible to compensate for this motion, thereby making digital subtraction techniques feasible for this application.

Another medical application may involve a comparison between vector fields computed in an area to represent brain shifts or other soft tissue deformations. Other possible medical applications may include but are not limited to monitoring the introduction of embolics into vascular aneurysms; introduction of cement into other bony anatomy; bone density analysis; etc. Analysis of bone morphogenic protein dispersion through the bone for spinal or orthopedic applications may be completed by looking at the slightest changes in bone density or other carrier with an image signature to monitor effectiveness or used to indicate or compute new dosages need to be administered. It is readily apparent from some of these examples that the time period between acquired image data may range from a few seconds to days or weeks.

While the invention has been described in its presently preferred form, it will be understood that the invention is capable of modification without departing from the spirit of the invention as set forth in the appended claims.

What is claimed is:

1. A medical imaging system to compare a first set of images and a second set of images, comprising:

a tracking subsystem having a dynamic reference frame marker configured to be physically attached to a patient, wherein the tracking subsystem is configured to detect the dynamic reference frame marker at both a first time to determine a first patient position data corresponding to a first set of images acquired with an imaging system and at a second time to determine a second patient position data corresponding to a second set of images acquired with the imaging system, where the first and second patient position data is indicative of a position of the patient, wherein the second time is after the first time;

a motion correction subsystem operable to receive the first patient position data relative to the imaging system at the first time and second patient position data relative to the imaging system at the second time corresponding to each of the first and second sets of images and the motion correction subsystem is operable to determine a change between at least the first patient position data and the second patient position data, wherein said motion correction subsystem is operable to execute an algorithm to compare the first patient position data and the second patient position data to determine a change between the first patient position data at the first time and the second patient position data at the second time and correct at least one of the first set of images or the second set of images for differences in at least one of position or orientation based on the determined change in the second patient position data relative to the first patient position data; and an image subtraction subsystem operable to receive at least the first set of images and the second set of images, the image subtraction subsystem is operable to perform a digital subtraction operation between the first set of images and the second set of images to determine a difference between the first set of images and the second set of images when no change equal to or less than a threshold value occurs between the first and second patient position data.

2. The medical imaging system of claim 1, wherein said tracking subsystem includes an optical tracking system, an electromagnetic tracking system, an acoustic tracking system, or combinations thereof;

wherein said tracking subsystem includes a tracking sensor selectively fixed to the patient and operable to be located by a localizer.

3. The medical imaging system of claim 1, wherein the first and second patient position data includes at least a two-dimensional representation of a position of a tracking sensor selectively affixed to the patient.

4. The medical imaging system of claim 1, wherein the first and second patient position data includes a three-dimensional representation relating to a position of a tracking sensor selectively affixed to the patient.

5. The medical imaging system of claim 1, further comprising:

a display to display the determined difference between the first set of images and the second set of images.

6. The medical imaging system of claim 1, wherein said image subtraction subsystem further includes an alert subsystem operable to alert a user that a change beyond the threshold value has occurred in the first and second patient position data.

7. The medical imaging system of claim 1, further comprising:
a third set of images and a third patient position data relating thereto to compare to the first set of images and the first patient position data relative thereto when a change beyond a threshold value has occurred between the first patient position data relating to the first set of images and the third patient position data relating to the third set of images.

8. The medical imaging system of claim 1, further comprising:
a surgical instrument tracked by the tracking subsystem;
wherein said motion correction subsystem is operable to correct the second set of images for motion artifacts caused by movement of the surgical instrument.

9. The medical imaging system of claim 1, wherein said threshold value is a maximum acceptable difference between the first patient position data relating to the first set of images and a device position data relating to the first set of images and that of the second patient position data and a device position data relating to the second set of images.

10. The medical imaging system of claim 9, wherein said motion correction system is further operable to correct the at least one of the first set of images or the second set of images for the determined change in the second patient position relative to the other of the first set of images or the second set of images when a change in the first and second patient position data is equal to or greater than the threshold value to correct at least one of the first set of images or the second set of images for the determined change in the second patient position data; and
wherein the image subtraction subsystem is operable to perform the digital subtraction operation between at least one of the first set of images and the second set of images and the corrected one of the first set of images and the second set of images.

11. The medical imaging system of claim 10, wherein the motion correction corrects for determined changes in patient position between the first patient position data relating to the first set of images and the second patient position data relating to the second set of images including at least one correction for a correction along a line perpendicular to an imaging axis, a correction along a line parallel to an imaging axis, a correction for rotation around an imaging axis, or combinations thereof.

12. The medical imaging system of claim 10, wherein the motion correction subsystem is operable to correct for scale, size, magnitude, direction, or combinations thereof relating to the first set of images and relating to the second set of images to allow for the image subtraction subsystem to form a digital subtraction operation between the first set of images and the second set of images.

13. The medical imaging system of claim 12, wherein the image subtraction subsystem is operable to perform a digital subtraction operation relating to the first set of images and the second set of images to illustrate only the differences between the first set of images and the second set of images for a procedure consisting of contrast angiography, contrast bone cement injection, soft tissue deformations, or combinations thereof.

14. The medical imaging system of claim 13, wherein the first set of images and the second set of images both include three dimensional image data;
wherein the motion correction subsystem is operable to compute a volume change of a contrast media as a function of time;
wherein a motion correction is applied to at least one of the first set of images or the second set of images and the computed volume change as the volume of the difference above a given intensity threshold between the first image set and the second image set;
wherein the computed volume change is constrained to lie within a segmented region of at least one of the first set of images or the second set of images.

15. The medical imaging system of claim 13, further comprising:
a tracked surgical instrument operable to be tracked by the tracking subsystem;
wherein the motion correction subsystem is operable to eliminate motion artifacts caused by changes in the position of the tracked surgical instrument by determining a region including the tracked surgical instrument using measured positions of the tracked surgical instrument relative to an imaging device that acquired the first set of images or the second set of images and data for the three-dimensional shape of the tracked surgical instrument and then eliminate instrument-induced motion artifact from the first set of images or the second set of images.

16. The medical imaging system of claim 1, wherein the first image data set or the second image data set is selected from fluoroscopic image data, magnetic resonance image data, X-ray image data, a computed tomography image data, an ultra-sound image data, or combinations thereof.

17. The medical imaging system of claim 1, wherein the first set of images or the second set of images is one dimensional image data, two dimensional image data, three dimensional image data, or combinations thereof.

18. A medical imaging system operable to capture two or more image sets representative of a patient, comprising:
a tracking subsystem configured to track a tracking marker fixed to the patient to detect a first patient position data, the tracking subsystem also configured to detect a first imaging device position data corresponding to a first image set at a first time and track the tracking marker fixed to the patient to detect a second patient position data and a second imaging device position data corresponding to a second image set at a second time different from the first time, where the first and second patient position data is indicative of a first and second position of a patient, respectively, and the first and second imaging device position data is indicative of a first and second position of an imaging device, respectively, at the first time and second time where the second time is later than the first time; and
a motion correction subsystem operable to receive the first patient position data relative to the imaging device and second patient position data relative to the imaging device from the tracking subsystem corresponding to each of the first image set and the second image set and the first imaging device position data and the second imaging device position data from the tracking subsystem corresponding to the first image set and the second image set, respectively, wherein the motion correction subsystem is operable to determine a change in relative position between the patient and the imaging device based upon the received first patient position data, first imaging device position data, second patient position data, and second imaging device position data, and, upon determining that the change in the relative position is equal to or greater than a threshold change value, compensate in at least one of the first image set or the second image set for the determined change in relative position, prior to an image subtraction subsystem performing a digital subtraction operation;

wherein the determined change in relative position is due to at least one of motion of the patient or motion of the imaging device between the first time and the second time;

wherein the compensation includes the motion correction subsystem correcting at least one of the first image set or the second image set based on the determined change.

19. The medical imaging system of claim 18, wherein the tracking subsystem further comprises:

a tracking sensor; and a tracking target connected to the tracking marker configured to be fixed to the patient and operable to be located by the tracking sensor;

wherein said tracking target is located via the tracking sensor to allow the tracking subsystem to determine at least one of the patient position data or the imaging device position data.

20. The medical imaging system of claim 18, wherein the tracking subsystem is an electromagnetic tracking subsystem, an acoustic tracking subsystem, an optical tracking subsystem, or combinations thereof.

21. The medical imaging system of claim 18, further comprising:

the imaging device that is operable to obtain the first image set including first images representative of the patient at the first time and the second image set including second images representative of the patient at the second time; and a tracking target connected to said imaging device trackable by said tracking subsystem so that said tracking subsystem is operable to determine a position of the imaging device when the first image set is obtained at the first time and when the second image set is obtained at the second time.

22. The medical imaging system of claim 21, further comprising:

a patient tracking target selectively attached with the tracking marker to the patient so that said tracking subsystem can determine the first and second patient position data for at least a portion of the patient relating to the first image set and the second image set.

23. The medical imaging system of claim 18, wherein said motion correction subsystem is operable to correct for a motion parallel to an axis of the imaging device, motion perpendicular to an axis of the imaging device, motion rotational relative to an axis of the imaging device, or combinations thereof.

24. The medical imaging system of claim 23, wherein the first and second patient position data and the first and second imaging device position data is substantially three dimensional so that the motion correction subsystem is operable to determine correction in at least three dimensions of the first image set or the second image set.

25. The medical imaging system of claim 18, further comprising:

a display; and an image subtraction subsystem operable to perform a digital subtraction operation between the first image set and the second image set;

wherein said image subtraction subsystem is operable to subtract at least one of the first image set or the second image set from at least one of the other of the second image set, the first image set, a corrected first image set, or a corrected second image set to create a resultant image data set;

wherein the resultant image data set is operable to be displayed on the display.

26. The medical imaging system of claim 18, where the first image set and the second image set relates to a soft tissue movement procedure, a bone cement placement procedure, a contrast angiography procedure, or combinations thereof.

27. The medical imaging system of claim 18, wherein the threshold value is a maximum acceptable difference between the patient position data relating to the first image set and the imaging device position data relating to the first image set and that of the second patient position data or the second imaging device position data of the second image set.

28. The medical imaging system of claim 18, wherein both of the first image set and the second image set is selected from fluoroscopic image data, magnetic resonance image data, X-ray image data, a computed tomography image data, an ultra-sound image data, or combinations thereof.

29. The medical imaging system of claim 18, wherein the first image set or the second image set is one dimensional image data, two dimensional image data, three dimensional image data, or combinations thereof.

30. The medical imaging system of claim 18, wherein the first set of images and the second set of images are both three dimensional image data;

wherein the motion correction subsystem is operable to compute volume changes of a contrast media as a function of time;

wherein a motion correction is applied to at least one of the first set of images or the second set of images and the computed volume change as the volume of the difference above a given intensity threshold between the first image set and the second image set;

wherein the computed volume change is constrained to lie within a segmented region of at least one of the first image set or the second image set.

31. The medical imaging system of claim 18, further comprising:

a tracked surgical instrument operable to be tracked by the tracking subsystem;

wherein the motion correction subsystem is operable to eliminate motion artifacts caused by changes in the position of the tracked surgical instrument by determining a region including the tracked surgical instrument using measured positions of the tracked surgical instrument relative to the imaging device and data for the three-dimensional shape of the tracked surgical instrument and then eliminate instrument-induced motion artifact from the first set of images or the second set of images.

32. A method for performing a digital subtraction operation in a medical imaging device, comprising:

determining a first patient position data with a tracking system, the first patient position data indicative of a first position of a patient relative to an imaging system during an acquisition of a first image set at a first time;

determining a second patient position data with the tracking system, the second patient position data indicative of a second position of the patient relative to the imaging system during an acquisition of a second image set at a second time later than the first time;

determining if a change equal to or greater than a threshold value occurs in between the determined first patient position data and the second patient position data during a time interval between the acquisition of the first image set and the acquisition of the second image set based at least on the determined first patient position data and the detected second patient position data;

performing a motion correction on at least the first image set or the second image set if the determined change is equal to or greater than the threshold value, wherein the motion correction includes correction for motion parallel to an axis of the first image set or the second image set, motion perpendicular to an axis of the first image set or the second image set, motion rotational around the axis of the first image set or the second image set, or combinations thereof determined as a position change of the patient relative to an image device that acquired the respective first image set and second image set; and performing a digital subtraction operation between the first image set and the second image set when the determined change is within the threshold value between one of the first image set and the corrected second image set or the second image set and the corrected first image set.

33. The method of claim 32, wherein capturing a first image set or capturing a second image set includes obtaining image data of the patient based on x-ray image data, fluoroscopy image data, magnetic resonance imaging data, ultrasound imaging data, a computed tomography image data, or combinations thereof.

34. The method of claim 32, wherein detecting a first patient position data and a second patient position data includes capturing patient position data for at least two dimensions relative to the patient.

35. The method of claim 32, wherein detecting a first patient position data and detecting a second patient position data includes detecting patient position data for three dimensions to describe a position of the patient.

36. The method of claim 35, further comprising:
correcting at least the first image set or the second image set based upon the determined change in a position of the patient in regards to rotation relative to the axis along which the image data sets first image set and the second image set are obtained.

37. The method of claim 32, further comprising:
detecting a first device position data indicative of the position of an imaging device during acquisition of the first image set;
detecting a second device position data indicative of the position of the imaging device during the acquisition of the second image set; and
determining if a change occurs in a position of the imaging device during a time interval between the acquisition of the first image set and the acquisition of the second image set.

38. The method of claim 37, further comprising:
determining if a relative position change occurs between the patient and the imaging device during a time interval between the acquisition of the first image set and the acquisition of the second image set.

39. The method of claim 38, further comprising:
performing a motion correction to at least one of the first image set or the second image set if a change is determined to have occurred in the relative position between the patient and the imaging device during the time interval between the acquisition of the first image set and the acquisition of the second image set.

40. The method of claim 32, further comprising:
creating a resultant image data set based upon the digital subtraction operation between the first image set and the second image set.

41. The method of claim 40, further comprising:
displaying the resultant image data set.

42. The method of claim 41, wherein the resultant image data set is illustrative of a contrast angiography, a positioning of a bone cement, a movement of a soft tissue in a patient, or combinations thereof.

43. The method of claim 32, further comprising:
capturing a third image set representative of the patient;
detecting a third patient position data indicative of the position of the patient during the acquisition of the third image set;
determining if a change occurs in a position of a patient during a time interval between the acquisition of the first image set and the acquisition of the third image set;
wherein the capturing of the third image set is performed when a change is determined to have occurred in a position of the patient during a time interval between the acquisition of the first image set and the acquisition of the second image set.

44. The method of claim 32, wherein capturing a first image set or capturing a second image set includes obtaining image data of the patient in at least one dimension image data, two dimension image data, three dimension image data, or combinations thereof.

45. The method of claim 32, further comprising:
injecting a contrast agent into the patient after capturing the first image, wherein the second image set is captured after injecting the contrast agent;
creating a resultant image data set based upon the performed digital subtraction; and
displaying the resultant image data set.

46. The method of claim 45, wherein determining if a change occurs in a position of the patient includes tracking the position of the patient with a tracking sensor at least between the first time and the second time.

47. The method of claim 46, wherein determining if a change occurs in a position of the patient includes tracking the position of the medical imaging device acquiring the first image set and the second image set with a tracking sensor at least between the first time and the second time.

48. The method of claim 45, wherein capturing the first set of images and the second set of images includes capturing three dimensional image data;
computing volume changes of the injected contrast media as a function of time within a segmented region in at least one of the first image set or the second image set;
correcting for motion in at least one of the first set of images or the second set of images and the computed volume change as the volume of the difference above a given intensity threshold.

49. The method of claim 32, further comprising:
tracking a surgical instrument;
eliminating motion artifacts caused by changes in the position of the tracked surgical instrument by determining a region including the tracked surgical instrument using measured positions of the tracked surgical instrument relative to an imaging device that acquired the first image set or the second image set and accessing data for the three-dimensional shape of the tracked surgical instrument and then eliminating instrument-induced motion artifact from the first set of images or the second set of images.

50. The method of claim 32, wherein the threshold value is a maximum acceptable difference between the patient position data relating to the first image set and an imaging device position data relating to the first image set and that of the second patient position data or a second imaging device position data of the second image set.

* * * * *